United States Patent [19]

Dickhudt et al.

[11] 4,276,882
[45] Jul. 7, 1981

[54] LEAD ANCHORING DEVICE

[75] Inventors: Eugene A. Dickhudt, St. Paul; Charles D. Ray, Long Lake, both of Minn.

[73] Assignee: Medtronic, Inc., Minneapolis, Minn.

[21] Appl. No.: 40,285

[22] Filed: May 18, 1979

[51] Int. Cl.$^3$ ............................................. A61N 1/04
[52] U.S. Cl. ................................. 128/419 P; 128/784;
128/DIG. 26
[58] Field of Search ........... 128/419 P, 419 C, 419 E,
128/784, 785, 786, 788, 419 R, DIG. 26

[56] References Cited

U.S. PATENT DOCUMENTS

| | | | |
|---|---|---|---|
| 3,244,174 | 4/1966 | Wesbey et al. | 128/419 P |
| 3,405,715 | 10/1968 | Hagfors | 128/784 |
| 3,461,869 | 8/1969 | Hargest | 128/DIG. 26 |
| 3,752,162 | 8/1973 | Newash | 128/419 P X |
| 3,880,169 | 4/1975 | Starr et al. | 128/419 P X |
| 4,029,103 | 6/1977 | McConnell | 128/DIG. 26 |

*Primary Examiner*—Lee S. Cohen
*Attorney, Agent, or Firm*—Schroeder, Siegfried, Ryan, Vidas, Steffey & Arrett

[57] ABSTRACT

An anchor for a body stimulation lead. A first body member is provided with an aperture while a second body member has a post extending from a surface thereof into the first body member aperture. At least the proximal portion of the post is slightly larger than the aperture to establish a press fit therein. Grooves are provided within one of the body members and are adapted to accept a body stimulation lead of known generally circular cross section. In a preferred embodiment, the groove opening is no greater than the lead diameter and the groove depth is at least as great as the lead radius. Suture cooperating elements are provided to facilitate securement of the anchor to body tissue.

10 Claims, 8 Drawing Figures

LEAD ANCHORING DEVICE

DESCRIPTION

1. Background of Prior Art

Electrical stimulation of the body is an increasingly important medical procedure. For example, the circumstances in which the well known cardiac pacemaker is employed have expanded considerably. Other electrical stimulators are similarly gaining in acceptance.

A difficulty encountered in many stimulating contexts is the requirement that the electrode be precisely positioned and that that position be maintained. For example, nerve stimulation is often selective requiring precision in the placement of the electrode. A later removement of the electrode is destructive of the effectiveness of the stimulation and may render the stimulation totally ineffective.

In some stimulating contexts, it is possible to secure the electrode in the desired position. In others, securement is not possible. In all stimulating contexts, forces acting on the lead may be transmitted by the lead to the electrode as a displacing force. Particularly in those contexts where the electrode is not secured, such forces have a tendency to displace the electrode.

Many surgeons have evolved their own techniques for anchoring a lead to reduce the transmittal of a displacing force to the electrode. For example, it is known that many surgeons employ a deformable surgical clip to anchor a body stimulator lead. The clip is positioned around and drawn down on the lead. The clip also engages body tissue thereby securing the lead to the body tisue. However, the nature of the engagement between the clip and the lead is potentially destructive to the lead, either at the time of placement or at a later time as a result of flexure of the lead. That is, the clip is crimped down on the lead such that the force imparted to the lead by the crimping action may damage the lead conductors.

Other lead anchoring techniques employ the use of materials which are known to dilate under the influence of other substances. For example, silicone rubber will dilate when placed in freon. This fact has been employed to devise a lead anchoring system in which a small section of a tube of silicon rubber having an inside diameter no larger than the outside diameter of the lead is placed in freon and dilated. In the dilated state, the lead is threaded through the silicone ring to the desired position. As the silicone returns to its natural state, it is fixed in position on the lead and may be employed as a suturing device.

The two systems described above, while providing an opportunity to secure a lead in position, have obvious drawbacks. For example, as stated above, the use of a surgical clip can result in damage to the lead. The silicone/freon system is extremely cumbersome, particularly in an operating room. Additionally, a small ring or band of silicone around the lead requires an encirclement of the lead with the suture, a practice discouraged by many surgeons, or a piercing of the band in close proximity to the lead, a practice having the potential of piercing the lead.

In abandoned Patent Application Ser. No. 926,105 filed July 19, 1978 in the name of Duane J. Zytkovicz for lead anchoring device which is commonly owned with the present invention, there is disclosed a lead anchoring system which overcomes many of the shortcomings of the prior art systems described above. The Zytkovicz teaching provides a body member having an aperture with a slot extending between the aperture and the surface of the body member. A portion of the lead is positioned in and engaged by the aperture with that engagement being enhanced by a force having a tendency to close the slot, as by a suture surrounding the body member, for example. Alternatively, the body member may be provided with tabs extending from the surface, one on either side of the slot. A suture through the tabs may be employed to enhance the engagement of the lead by the aperture as well as to provide a means for anchoring the lead at a position relatively remote from the lead. However, while it is an advance over many prior art techniques, the Zytkovicz anchoring system is somewhat cumbersome in that it often requires two hands to position it on the lead in situations where working space is limited.

2. Brief Summary of the Invention

The present invention provides a lead anchoring system which may be easily positioned on the lead and which can be urged into engagement with the lead with two fingers. The system consists essentially of first and second body members having opposing surfaces, one body member having an aperture and the other having a post extending into the aperture. At least the proximal portion of the post is slightly larger than the aperture to establish a press fit therein. A groove is provided within one of the body member opposing surfaces, one groove for each lead. The groove opening is no greater than the lead diameter and the groove depth is at least as great as the lead radius. In a preferred embodiment, the groove depth is at least as great as the lead diameter and approximates the lead diameter. With the post in the aperture, and the opposing surfaces spaced from each other, a lead may be threaded along the groove on one of the opposing surfaces. When that portion of the lead that it is desired to engage is between the opposing surfaces, a force is imparted to the body members as by a thumb and forefinger forcing them toward each other and the lead portion securely into the groove. Preferably, the groove opening is slightly less than the lead diameter which, in conjunction with a groove depth at least as great as the lead radius, results in a compressive force applied to the sides of the lead having a tendency to retain the lead within the groove in firm engagement. This force is independent of the body member opposing surface which forced the lead into the groove. Thus, the lead is firmly restrained within a groove in one body member opposing surface with the other body member opposing surface tending to maintain the lead in the groove but with the primary engagement between the lead and anchoring device being the engagement between the groove sides and the lead itself.

In a preferred embodiment, the body members are provided with suture holes which may be employed to secure the two body members to each other as well as to secure the anchor system to body tissue. A second post may be provided to extend from one of the opposing surfaces and into a suture hole of the other body member to establish and maintain alignment between the suture holes of one body member and those of the other. Preferably, the second post should be provided with a taper to ease assembly of the device.

DETAILED DESCRIPTION OF THE INVENTION

Figure 1:
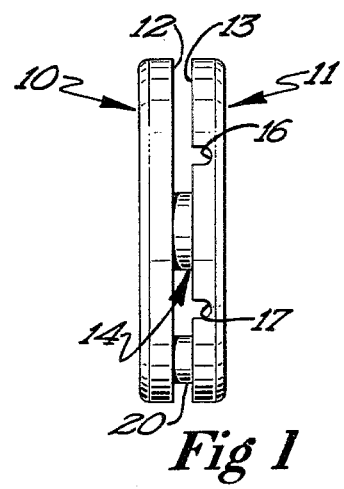
FIG. 1 is a side view illustrating a preferred embodiment of the present invention.

Referring now to FIG. 1, there is illustrated, in a side view, a preferred embodiment of the present invention formed by body members 10 and 11. Body members 10 and 11 are generally disc shaped having opposing surfaces 12 and 13, respectively. Body member 10 has a centrally located post 14 extending from the surface 12 into a central aperture 15 (see FIG. 5) in the body member 11. Grooves 16 and 17 are provided in the surface 13 of body member 11 and will be described more fully below. The body members 10 and 11 may be formed of any material suitable for the environment of the human body.

Figure 2:
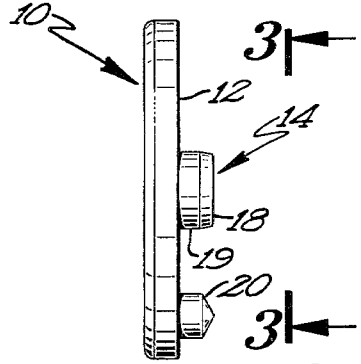
FIG. 2 is a side view of a body member forming a part of the embodiment of FIG. 1.
Figure 3:
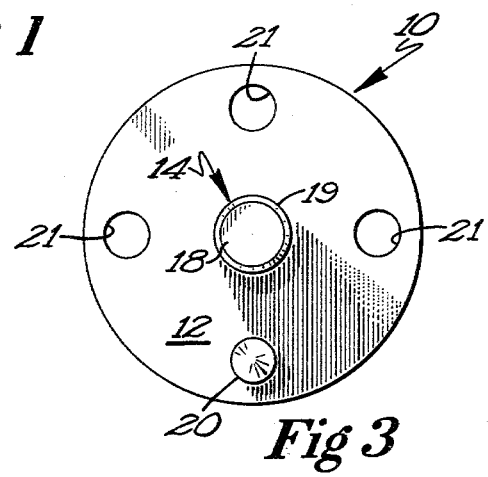
FIG. 3 is a view of the body member of FIG. 2 taken along the direction of the arrow 3 in FIG. 2.

FIGS. 2 and 3 better illustrate the body member 10 of FIG. 1. As illustrated, the post 14 has a taper at its distal or terminal portion 18. The distal portion 18 of the post tapers to a diameter slightly less than the diameter of the aperture 15 while the proximal portion 19 of post 14 has a diameter slightly larger than that of aperture 15 such that when the body members 10 and 11 are positioned relative to each other as illustrated in FIG. 1, and urged toward each other, a press fit is established between the proximal post portion 19 and the aperture 15. A second post 20, having a tapering distal or terminal end, projects from the surface 12 for purposes to be discussed more fully below. Suture holes 21 are provided through the body member 10 and will also be discussed more fully below.

Figure 4:
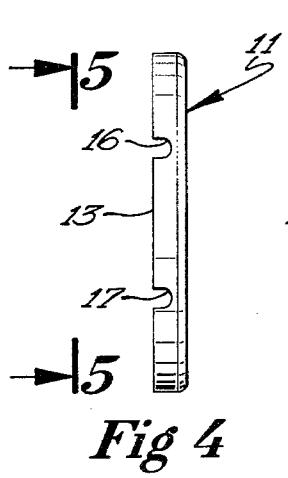
FIG. 4 is a side view of a body member forming a part of the embodiment of FIG. 1.
Figure 5:
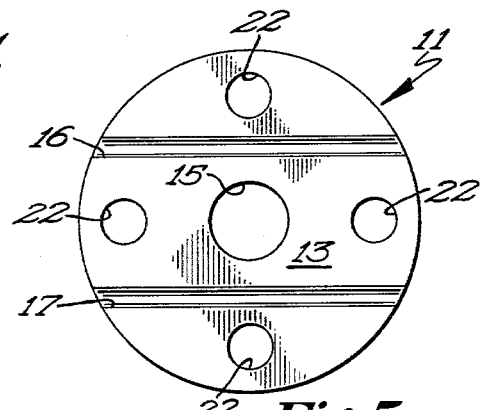
FIG. 5 is a view of the body member of FIG. 4 taken along the direction of the arrow 5 in FIG. 4.

FIGS. 4 and 5 better illustrate the body member 11 of FIG. 1. Suture holes 22 extend through the body member 11 around the periphery of the body member 11 and from the surface 13. Suture holes 22 are positioned such that three of them will be in alignment with the suture holes 21 of body member 10 when the post 20 is in the other of the suture holes 22 and the post 14 is in the aperture 15. Thus, post 20, in cooperation with one of the suture holes 22, facilitates the alignment of the suture holes 21 with three of the suture holes 22. The taper of post 20 facilitates positioning of the post 20 within one of the suture holes 22.

Figure 6:
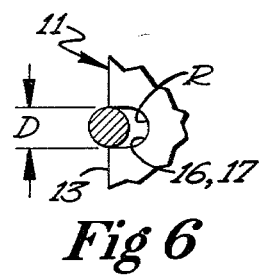
FIG. 6 illustrates a portion of the body member of FIG. 4 and its cooperation with the lead.

Referring again to FIG. 1, with the post 14 within the aperture 15 and the post 20 within one of the suture holes 22, and with the opposing surfaces 12 and 13 spaced from each other, as illustrated, a lead that it is desired to anchor may be threaded between the surfaces 12 and 13 to lie over one of the grooves 16 and 17. Preferably, the grooves 16 and 17 have a groove opening, dimension D in FIG. 6, that is no larger than the diameter of the lead it is desired to anchor and, more preferably, have a groove opening slightly smaller than the diameter of that lead. In addition, so that the forces acting on the lead do not have a tendency to expel the lead from the groove, the depth of the groove should be no less than the radius of the lead it is desired to anchor. Thus, the lead is accepted in the groove at least to the extent illustrated in FIG. 6 such that when the lead is urged into the groove the lead will be compressed between the side walls of the groove at its major dimension. Most preferably, the groove depth is at least as great as the lead diameter and approximates the lead diameter. The groove may be provided with a radius R which is equal to one half the groove opening D. With a lead overlying a groove, the surfaces 12 and 13 may be moved toward each other by a force applied to the body members 10 and 11, with the thumb and forefinger, for example. The lead is then urged into the groove to the extent of the groove depth. The press fit between post 14 and aperture 15 will maintain the surfaces 12 and 13 in close proximity.

Figure 7:
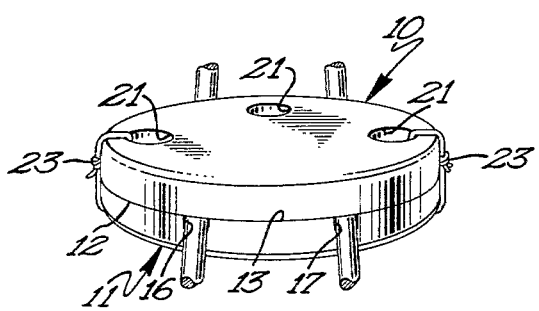
FIG. 7 illustrates one configuration of a preferred embodiment of the present invention.
Figure 8:
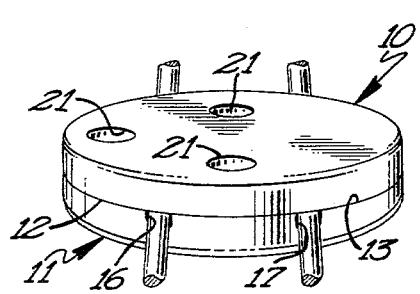
FIG. 8 illustrates an alternative configuration of a preferred embodiment of the present invention.

FIGS. 7 and 8 illustrate alternative configurations of the body members 10 and 11. In FIG. 7, the post 20 of body member 10 is positioned within one of the suture holes 22 that lies between the grooves 16 and 17. In FIG. 8, the post 20 is in one of the suture holes 22 that does not lie between the grooves 16 and 17. As can be seen, these different configurations allow a different relationship between the suture holes 21, and the aligned associated suture holes 22, with the leads to be anchored by the system of the present invention. Four different configurations are possible, with the selected one being that that is most advantageous in a particular situation.

Many modifications and variations of the present invention are possible in light of the above teachings. For example, as many grooves may be provided as there are leads it is desired to anchor. In most situations, there will be two leads each having an associated electrode. In addition, the body members 10 and 11 may be secured to each other as by sutures passed through the suture holes 21 and 22 as illustrated at 23 in FIG. 7. This will provide a safety margin against separation of the body members in the event that the press fit between the post 14 and aperture 15 does not hold. It is therefore to be understood that, within the scope of the appended claims, the invention may be practiced otherwise than as specifically described.

We claim:

1. An anchor for a body stimulation lead which comprises:
   first and second body members having opposing surfaces;
   an aperture within said first body member;
   a post extending from said opposing surface of said second body member into said first body member aperture, at least a portion of said post being slightly larger than said aperture to establish a press fit therein;
   at least one groove within at least one of said body member opposing surfaces, said groove having a groove opening and a groove depth and being adapted to accept a body stimulation lead of known generally circular cross section, the groove opening being no greater than the lead diameter and the groove depth being at least as great as the lead radius; and
   suture cooperating means within said first and second body members.

2. The lead anchor of claim 1 wherein said groove depth approximates the lead diameter.

3. The lead anchor of claim 1 wherein said groove depth is at least as great as the lead diameter.

4. The lead anchor of claim 1 further comprising means for facilitating the alignment of the suture cooperating means of one body member with the suture cooperating means of the other body member.

5. The lead anchor of claim 4 wherein said suture cooperating means comprise suture holes, said alignment facilitating means comprising means carried by one of said body members for engaging a suture hole of the other body member.

6. The lead anchor of claim 5 wherein said alignment facilitating means comprises a tapering post.

7. The lead anchor of claim 6 wherein said tapering post is carried by said second body member.

8. The lead anchor of claim 5 wherein all grooves are in said first body member.

9. The lead anchor of claim 1 wherein said body members are generally disc shaped and normally spaced from each other, said body members being movable toward each other to establish said press fit.

10. The lead anchor of claim 1 wherein all grooves are in said first body member.

* * * * *